United States Patent [19]

Breuer et al.

[11] Patent Number: 4,885,289

[45] Date of Patent: Dec. 5, 1989

[54] ALTERATION OF CHARACTER OF MALE BEARD GROWTH

[76] Inventors: Miklos M. Breuer, 108 Ridge Ave., Newton, Mass. 02159; Edwin G. Kaszynski, 12928 Dean Rd., Wheaton, Md. 20902; Douglas Shander, 5 Meadowgrass Ct., Gaithersburg, Md. 20878; Vera R. Usdin, 6 Stevens Ct., Rockville, Md. 20850; Hermes van der Lee, 4630 Thornhurst Dr., Olney, Md. 20832

[21] Appl. No.: 807,623

[22] Filed: Dec. 11, 1985

Related U.S. Application Data

[63] Continuation-in-part of Ser. No. 560,726, Dec. 12, 1983, abandoned.

[51] Int. Cl.$^4$ .................. A61K 31/56; A61K 31/585
[52] U.S. Cl. ............................. 514/170; 514/175; 514/177; 514/178; 514/179
[58] Field of Search ............... 514/170, 175, 177, 178, 514/179

[56] References Cited

U.S. PATENT DOCUMENTS

| | | | |
|---|---|---|---|
| 3,426,137 | 2/1969 | Philpitt et al. | 414/330 |
| 4,039,669 | 8/1977 | Beyler et al. | 424/243 |
| 4,098,802 | 7/1978 | van der Vies | 260/397.4 |
| 4,139,638 | 2/1979 | Neri et al. | 424/324 |
| 4,161,540 | 7/1979 | Neri et al. | 424/324 |
| 4,191,775 | 3/1980 | Glen | 424/304 |
| 4,269,831 | 5/1981 | Ferrari et al. | 424/241 |
| 4,272,508 | 6/1981 | Tamm | 424/45 |
| 4,310,523 | 1/1982 | Neumann | 424/240 |
| 4,344,941 | 8/1982 | Wiechert et al. | 424/243 |
| 4,367,227 | 1/1983 | Bingham | 424/243 |
| 4,370,315 | 1/1983 | Greff et al. | 424/94 |
| 4,439,432 | 3/1984 | Peat | 424/240 |
| 4,684,635 | 8/1987 | Orentreich et al. | 514/175 |

FOREIGN PATENT DOCUMENTS 2840144  3/1980  Fed. Rep. of Germany.
58-57308  4/1983  Japan.

OTHER PUBLICATIONS

Burdick, et al: "*The Topical Effect of the Antiandrogen Chlormadinone Acetate and Some of Its Chemical Modifications on the Hamster Costovertabral Organ*", Br. J. Derm. (1970) 82, Supplement 6, 19.

Simpson, et al: "*The Effect of Topically Applied Progesterone on Sebum Excretion Rate*", British Journal of Dermatology (1979) 100, 687.

Girard, et al: "*Inhibition of Testosterone Metabolism and Lipogenesis in Animal Sebaceous Glands by Progesterone*", Arch Dermatol Res 269, 281–290 (1980).

Goos, et al: "*An Improved Method for Evaluating Antiandrogens*", Arch Dermatol Res (1982) 273:333–341.

*Primary Examiner*—D. W. Robinson
*Assistant Examiner*—Joseph A. Lipovsky

[57] ABSTRACT

The rate and character of androgen-stimulated beard hair growth in intact, sexually mature males is altered by the topical application out of a dermatologically acceptable carrier of an antiandrogen material. In a preferred practice of the invention, compositions containing both a steroid 5-alpha-reductase inhibitor and a cytoplasmic androgen receptor binding agent are employed.

26 Claims, No Drawings

ALTERATION OF CHARACTER OF MALE BEARD GROWTH

This application is a continuation-in-part of our copending application Ser. No. 560,726, filed Dec. 12, 1983, now abandoned.

This invention relates to a new and novel approach in the alteration of the rate and the character of androgen-stimulated hair growth by the topical application of compositions containing materials selected from the group consisting of 5-alpha-reductase inhibitors and cytoplasmic androgen receptor binding agents.

BACKGROUND OF THE INVENTION

A great deal of medical investigation has been directed to the elucidation of the role of the endocrine system in the growth of human hair. As the result of such investigations, it is generally agreed that the fine, lightcolored vellus hair, which covers most of the body during childhood, comes under the influence of growth hormone and of androgens to eventually become the coarser and darker terminal hairs which characterize many areas of the adult body.

In each body area, the character of the final hair growth is determined not only by the level of circulating androgen and the sensitivity of the follicles in that area to androgen, but also to the length of time over which the follicles have been exposed. Both pubic and axillary hair appear early in puberty but decrease with the onset of the androgen deficiency of old age. Beard growth and balding, on the other hand, develop late in puberty and outlast the natural diminution of androgen. The desired to discover methods for controlling androgen-dependent conditions has generated a large number of studies dealing with androgen metabolism in skin.

As a result of these studies, it is thought that all steroids, including testosterone, the principal androgen circulating in the plasma in men, enter target tissues by passive diffusion. In some tissues, such as muscle, testosterone binds directly to a cytoplasmic receptor protein permitting translocation of the hormone into the cell nucleus. Once inside, the testosterone-receptor complex brings about synthesis of new proteins necessary for expression of virilizing activities by the cell.

In other tissues, such as skin, intracellular testosterone is first reduced by the enzyme steroid 5-alpha-reductase to the compound dihydrotestosterone before association with the receptor and subsequent nuclear translocation takes place. Thus, in the treatment of androgen-mediated conditions in skin, it is possible to reduce the amount of androgen capable of entering the nucleus by two means.

Firstly, the conversion of serum testosterone to dihydrotestosterone can be prevented by the inhibition of the enzyme steroid 5-alpha-reductase. Secondly, certain compounds can compete with the testosterone or dihydrotestosterone for the cytoplasmic receptor sites. Our invention is the first to demonstrate altering the rate and character of beard hair growth by topical application of antiandrogens (5-alpha-reductase inhibitors and/or cytoplasmic receptor binding agents) in adult males. The action of such antiandrogen compounds in skin can also affect the output of sebaceous glands and the course of male pattern hair growth in females, thus leading to their application in the treatment of acne and female hirsutism. The ideal anti-androgenic agent for purposes of altering beard hair growth is one which is active topically with no significant side effects. Although several topically active antiandrogens have been reported in the art, none claim or teach an effect on the rate and character of male beard hair growth.

U.S. Pat. No. 4,039,669 describes the topical use of 17-alpha-R-androst-4-en-17-beta-ol-3-one or esters thereof where the R is n-propyl or n-butyl for the control of dermatological conditions associated with androgen-mediated conditions such as acne.

U.S. Pat. Nos. 4,139,638 and 4,161,540 describe the use of certain 4'-substituted and 3',4'-disubstituted anilides for the treatment of androgen-dependent disease states such as female hirsutism and acne.

U.S. Pat. No. 4,191,775 discloses that certain 3,4-disubstituted branched-chain fluorinated acylanilides may be used in the topical treatment of androgen-dependent disease conditions such as acne, female hirsutism, and seborrhoea.

U.S. Pat. No. 4,344,941, describes the topical use of certain androgenic 17-alpha-substituted steroids exemplified by 17-beta-hydroxy-1-alpha-methyl-17-alpha-(1-methyl-2-propenyl)-5-alpha-androstan-3-one for the treatment of diseases such as acne, seborrhoea, alopecia and female hirsutism.

U.S. Pat. No. 4,367,227 describes a cosmetic composition for reducing sebum secretion from the skin comprising alcoholic solutions of cyproterone acetate.

West German OLS 2,840,144 describes the use of combination of progesterone with either cyproterone acetate or chlormadinone acetate in the topical treatment of androgeninduced hormonal disturbances such as alopecia, female hirsutism, and acne.

Japanese Kokai 58-57308 describes the restoration of hair to bald heads by the topical applications of oxidizing substances such as stabilized chlorine dioxide, potassium bromate, or ozone to supress the enzymatic activity of the reductive enzyme 5-alpha-reductase.

The patent art discloses a number of ways of reducing the growth of human hair as opposed to its conventional removal by cutting, shaving, or depilation. One such method is described in U.S. Pat. No. 3,426,137, which pertains to a process for inhibiting the growth of hair by the topical application to a depilated skin area of a composition containing a substituted benzophenone such as 2-amino-5-chloro-benzophenone. Examples in the patent illustrate the reduction of hair growth on the back area of rabbits and on the arm of a male human subject.

Another process for extending the duration of depilation is described in U.S. Pat. No. 4,370,315. The process therein comprises the topical application of a composition containing a lipoxygenase along with linoleic acid or derivative thereof. The patent describes the application of such composition to various body parts of female human subjects in the majority of which regrowth of hair was clearly perceptible only after six or more weeks.

In U.S. Pat. No. 4,439,432 topical compositions containing progesterone are reported for use in treatment of progesterone deficiency and related conditions, including abnormal hair growth resulting from androgen excess. Further insights on this point may be obtained from the related literature, among which mention may be made of Simpson et al. "The Effect of Topically Applied Progesterone on Sebum Excretion Rate," *Br. J. Derm.*, 100, p. 687 (1979), in which progesterone was reported effective in reducing sebum excretion rates in females, but without effect in males. In Goos et al, "An Improved Method for Evaluating Antiandrogens,"

Arch. Dermatol. Res., 273, pp. 333-341 (1982), the effect of progesterone on inhibition of hair growth in intact males is doubtful (p. 340, Table 3, Group VI vs. Group X). In Burdick et al, "The Topical Effect of the Antiandrogen Chlormadinone Acetate and Some of Its Chemical Modifications on the Hamster Costovertebral Organ," Br. J. Derm., 82, Supplement 6, p. 19 (1970), antiandrogens were either ineffective or of questionable effect in inhibiting flank organ function in normal intact male hamsters. Similarly, in Girard et al, "Inhibition of Testosterone Metabolism and Lipogenesis in Animal Sebaceous Glands by Progesterone," Arch. Dermatol. Res., 269, pp. 281-290 (1980), progesterone is found effective in the female but not in the male. In all of the above experiments topical antiandrogens were ineffective in males in inhibiting androgenic function. When the female and male responses were compared in both humans and hamsters, only females responded to topical treatment.

In U.S. Pat. No. 4,269,831 a substantial reduction in hair growth of the hamster flank organ is among the effects reported from topical application of 17β-hydroxy-17α-propylandrost-4-en-3-one. However reduction in the size of the flank organ is also described, leaving a smaller field on which the hair can grow. Therefore, the reduction in hair growth may be a consequence of a decrease in area of the flank organ rather than an alteration in the character of the hair.

SUMMARY OF THE INVENTION

We have now discovered that antiandrogen materials of two classes, namely steroid 5-alpha-reductase inhibitors and cytoplasmic androgen receptor binding agents may be employed in altering the rate and character of androgen-stimulated hair growth in the beards of intact, sexually mature males. Concomitant histological changes are observed, as well as reduction in hair cutting forces, so as to facilitate a shaving operation. The antiandrogens are applied topically out of a dermatologically acceptable carrier for local effect and with minimal alteration of other androgen-mediated bodily functions through systemic action. In a preferred practice of the invention, compositions containing both a steroid 5-alpha-reductase inhibitor along with a cytoplasmic androgen receptor binding agent are employed.

DETAILED DESCRIPTION OF THE INVENTION

We have discovered that the normal rate of male beard hair growth can be reduced and its character caused to revert toward the vellus state, with accompanying reduction in cutting force, by the topical application of antiandrogen compounds of either the 5-alpha-reductase inhibitor type or the cytoplasmic androgen receptor binding agent type. By the proper selection of antiandrogen compound and its mode of use, unwanted interference with other androgen mediated bodily processes can be minimized or avoided.

The absence of antagonism of systemic androgen activity in the practice of our invention can be shown by the topical application of suitable compositions to one of the two flank organs of mature male hamsters. Dose-related decreases in androgen-dependent flank organ hair growth are obtained on the treated side but no statistically significant change occurs on the contralateral, vehicle-treated side. Similar studies have been conducted using female hamsters in which hair growth on the flank organs has been stimulated by the subcutaneous administration of a suitable androgen.

A novel method for screening topical antiandrogens has been developed in which the fluctuations in flank organ activity of the enzyme ornithine decarboxylase (ODC) in response to androgens and antiandrogens is exploited to provide a rapid, invivo screen for antiandrogens, based on a biochemical parameter specifically related to androgenic stimulation of pilosebaceous target tissues. In several studies, unilateral topical application of the antiandrogens 17α-propyltestosterone and 17α-allyltestosterone selectively decreased ODC activity in treated but not untreated flank organs of intact (i.e. uncastrated) male hamsters. Treatment of androgen-stimulated female hamsters with topical cyproterone acetate or progesterone also inhibited ODC activity.

A further series of investigations on the androgenic regulation of ODC activity in hamster flank organs has been conducted to test topical antiandrogenic formulations consisting of combination regimens. Antiandrogens, both androgen-binding inhibitors (examples being cyproterone acetate, chlormadinone acetate, 17α-propyltestosterone, and 17α-allyltestosterone) and 5-alpha-reductase inhibitors such as progesterone, were found to inhibit ODC activity in flank organs when applied topically. However, the combination of progesterone with binding inhibitors enhanced the magnitude of ODC inhibition and allowed a reduction of the dose of binding inhibitors necessary for maximal local efficacy. Combination formulations containing low doses of androgen-binding inhibitors appeared to be the most effective topical antiandrogens producing high local and low contralateral effects. Combinations containing progesterone and 17α-propyltestosterone or 17α-allyltestosterone provided maximal local inhibition and, in contrast to other regimens, did not cause any contralateral effects.

Summarized below are the results of several experiments comparing the efficacy of several compositions in reducing the flank organ hair mass of adult intact male hamsters. In each case, hamsters (ten animals per treatment group) were treated for 15 days (Monday-Friday) during a 21-day interval. Flank organ hairs were depilated on the first day of treatment and redepilated on the sixth day of treatment. The mass of flank organ hair represents the regrowth during the final 14 days of the 21-day interval. The results for percent inhibition shown below are based upon comparisons between the hair mass values of hairs harvested from treated flank organs of experimental animals and those obtained from vehicle-treated control animals.

| Steroidal Antiandrogen(s) | Experiment I Rate of Application in Micrograms per Square Centimeter | % Inhibition |
|---|---|---|
| Progesterone | 1000 | 30 |
| Cyproterone acetate | 500 | 26 |
| 17α-Propyltestosterone | 6 | 26 |
| 17α-Propyltestosterone + Progesterone | 6 1000 | 39 |
| Cyproterone acetate + Progesterone | 500 1000 | 52 |

| Experiment II | | |
|---|---|---|
| Steroidal Antiandrogen(s) | Rate of Application in Micrograms Per Square Centimeter | % Inhibition |
| Cyproterone acetate | 500 | 38 |
| Cyproterone acetate | 50 | 23 |
| 4-androstene-3-one-17β-Carboxylic acid | 400 | 29 |
| Cyproterone acetate + 4-androstene-3-one-17β-Carboxylic acid | 50 400 | 41 |
| Cyproterone acetate + 4-androstene-3-one-17β-Carboxylic acid | 500 400 | 54 |

| Experiment III | | |
|---|---|---|
| Steroidal Antiandrogen(s) | Rate of Application in Micrograms Per Square Centimeter | % Inhibition |
| Progesterone | 1000 | 57 |
| Spironolactone | 500 | 41 |
| Chlormadinone acetate | 500 | 45 |
| Chlormadinone acetate + Progesterone | 500 1000 | 69 |

| Experiment IV | | |
|---|---|---|
| Steroidal Antiandrogen(s) | Rate of Application in Micrograms Per Square Centimeter | % Inhibition |
| Progesterone | 1000 | 48 |
| 17α-allyltestosterone | 5 | 0 |
| 17α-allyltestosterone | 20 | 29 |
| 17α-allyltestosterone | 50 | 50 |
| 17α-allyltestosterone | 100 | 50 |

| Experiment V | | |
|---|---|---|
| Steroidal Antiandrogen | Rate of Application in Micrograms Per Square Centimeter | % Inhibition |
| 17α-allyltestosterone | 25 | 37 |
| 17α-allyltestosterone | 100 | 59 |
| 17α-allyltestosterone | 400 | 59 |

| Experiment VI | | |
|---|---|---|
| Steroidal Antiandrogen | Rate of Application in Micrograms per Square Centimeter | % Inihibition |
| Progesterone | 100 | 34 |
| Progesterone | 500 | 32 |
| 17α-allyltestosterone | 25 | 40 |
| Progesterone + 17α-allyltestosterone | 500 + 25 | 54 |

EXPERIMENT VII

Following the same three-week treatment regimen as described for Experiments I–VI, a group of intact, mature male hamsters was treated with a combination of 17α-allyl-testosterone and progesterone at dosage rates of 10 and 200 μg/cm², respectively. At the end of the treatment period the animals were sacrificed, and their flank organs excised and subjected to histological examination. It was found that the treatment did not markedly affect the growth phase of the hair follicles, i.e., they continued to produce hair, but the nature of the hair was modified. Specifically, the hairs were noticeably finer than on the control (vehicle-treated) side; the medulla portion of the hair and a more orderly structure than in intact control animals, more nearly like the structure observed in castrates; and the follicles of treated animals were noticeably reduced in size, but not to the extent observed in castrates.

EXPERIMENT VIII

This experiment measured the effect of treatment according to the invention on the force required to cut the affected hair. The same three-week regimen was followed as in the previous experiments, this time using 17α-allyl-testosterone alone at a dosage rate of 100 μg/cm². The treatment resulted in 48% inhibition of hair growth, measured with a group of six animals.

The apparatus for measuring the cutting force comprises a razor blade (Gillette "Super Stainless") mounted in an electromechanical force-measuring device, adapted to use a fresh portion of the cutting edge for each cut through a hair. The hair is cut against an anvil, with a read-out of the maximum force exerted, which occurred just as the hair was cut through. A smooth rise in cutting force to a maximum, followed by a sharp drop-off, indicated that the hair under the cutting edge was flat against the anvil and the reading was a valid measure of force to cut the hair. If the hair under the cutting edge is bowed, the force curve is distorted, and the reading is discarded. In practice about ten hairs were typically required to obtain seven valid readings.

The hairs to be measured were first held in a humidity-controlled environment (22° C., 65% relative humidity) for 48 hours before cutting. In order to eliminate any possibility of bias in the test, the thickest hairs from both the untreated and treated sides of test animals were selected for cutting, even though the proportion of thick hairs on the treated sides were fewer in number as compared to the control sides. Results of the cutting force experiment are presented in the following table.

| Treatment Group | Number of Animals | Number of Hairs Per Animal | Total | Cutting Force, Grams Mean | S.E.M. |
|---|---|---|---|---|---|
| Control Flank Organ Hairs | 6 | 7 | 42 | 0.983 | ± .046 |
| Treated With 17α-allyltestosterone | 6 | 7 | 42 | 0.567 | ± .029 |

The difference in cutting force thus measured is significant at or above the 99% confidence level.

In employing the topical application of antiandrogens in altering the rate and character of bear hair growth, one may use a variety of 5-alpha-reductase inhibitors and cytoplasmic receptor binding agents either alone or in combination with each other. Among the 5-alpha-reductase inhibitors that may be employed are progesterone; (5α,20-R)-4-diazo-21-hydroxy-20-methyl pregnan-3-one; (4R)-5,10-seco-19-norpregna-4,5-diene-3,10,20-trione; 4-androstene-3-one-17β-carboxylic acid, and its methyl ester; 17β-N,N-diethylcarbamoyl-4-methyl-4-aza-5α-androstane-3-one; 11α-hydroxyprogesterone;; 17α-hydroxy-progesterone; and 20α-hydroxyprogesterone. For minimum alteration of other androgen-mediated bodily functions through systemic action, we prefer to use progesterone or 4-androstene-3-one-17- carboxylic acid. The concentration and level of application of these materials in formulated compositions as discussed below should be such that from about 10 to about 10,000 micrograms of active material per square centimeter of skin will be applied. We prefer compositions which will result in the application of about 100 to about 1,000 micrograms per square centimeter.

Among the cytoplasmic receptor binding agents which may be mentioned are cyproterone acetate, chlormadinone acetate, $17\alpha$-propyltestosterone, $17\alpha$-allyltestos-terone,$\alpha,\alpha,\alpha$-trifluoro-2-methyl-4'-nitro-m-propionotoluidide; $6\alpha$-bromo-$17\beta$-hydroxy-$17\alpha$-methyl-4-oxa-$5\alpha$-androstane-4-one; $17\beta$-acetoxy-$4\alpha$,5-cyclo-A-homo-B-nor-$5\alpha$-androst-1-ene-3-one; and spironolactone. For minimal alteration of other androgen-mediated bodily functions through systemic action we prefer to use $17\alpha$-propyltestosterone or $17\alpha$-allyltestosterone. The concentration and level of application of these materials in formulated compositions as discussed below should be such that from about 0.1 to 5,000 micrograms of active material per square centimeter of skin will be applied. We prefer compositions which result in the application of about 1.0 to 500 micrograms per square centimeter.

We prefer to employ 5-alpha-reductase inhibitors and cytoplasmic androgen receptor binding agents in combination with each other because the 5-alpha-reductase inhibitors appear to enhance the action of the cytoplasmic androgen receptor binding agents, permitting a lower concentration to be used, thus reducing the risk of systemic side effects. When used in combination, the 5-alpha-reductase inhibitors and cytoplasmic androgen receptor binding agents should be employed within the ranges of application discussed above for separate use of the 5-alpha-reductase inhibitors and cytoplasmic androgen receptor binding agents.

In formulating the compositions to be applied topically in the practice of this invention, any dermatologically acceptable base or carrier may be employed. Care should be taken, however, to use a base or carrier which will provide uniform localized absorption of the antiandrogen principle without significant systemic absorption. The art practiced in the formulation of skin creams for cosmetic purposes may usefully be employed in the formulation of compositions used in the practice of our invention. For example, many derivatives of lanolin are known to have excellent emulsifying properties and may be used to facilitate the formulation of emulsions having critical stability requirements. Lanolin has also been thought to aid in the absorption of active materials into the skin. While the active materials may be incorporated in a variety of cosmetic-based materials such as simple solutions, creams, suspensions, gels and the like, water-in-oil type cream emulsions may offer advantages in that the continuous oil phase provides direct contact with the lipids of the skin to provide a route for slow continuous absorption of the active antiandrogen.

In formulating compositions containing 5-alpha-reductase inhibitors, it is possible to include as little as 0.1% or as much as 10.0% by weight in the practice of our invention. We prefer to use from 1.0 to 4.0% by weight. In formulating compositions containing cytoplasmic receptor binding agents, it is likewise possible to use from 0.1 to 10.0% by weight. We prefer, however, to use from 0.5 to 5.0% by weight in the case of cyproterone acetate, chlormadinone acetate, and spironolactone and from 0.02 to 0.5% by weight in the case of other cytoplasmic receptor binding agents.

In using the antiandrogen-containing compositions described herein in altering human beard growth, sufficient quantity of the composition is rubbed into the bearded area of the skin of the face and neck preferably on a daily basis to provide the level of application discussed above. Continued use will result in a reduction of beard hair mass and a gradual reversion toward the vellus state, along with a reduction in cutting forces so as to facilitate a shaving operation. The maximum rate of change which will be achieved will vary from individual to individual.

The following examples are illustrative of compositions to be used in the practice of the invention but are not to be construed as limiting.

EXAMPLE 1 - SKIN LOTION

| Ingredients | Weight % |
|---|---|
| Progesterone | 2.2 |
| Cetyl Alcohol | 4.0 |
| Mineral Oil | 4.0 |
| Isopropyl Myristate | 1.0 |
| Dimethicone | 1.0 |
| Lanolin Alcohol | 0.5 |
| Glycerol monostearate | 1.0 |
| Sodium lactate (60% aq. soln.) | 1.4 |
| Dimethyl diammonium chloride (75% active)-Arquad 2HT75* | 2.0 |
| Propylene glycol | 3.0 |
| Methyl paraben | 0.2 |
| Propyl paraben | 0.1 |
| Titanium dioxide | 0.1 |
| Perfume | 0.1 |
| Water | 79.4 |
| | 100.0 |

*Armak Co., McCook, Illinois

PROCEDURE

Deionized water and propylene glycol are heated to 70° C. Methyl paraben is added under high shear agitation. In another container combined emollient oils, emulsifier, prewarmed dimethyl diammonium chloride, active ingredients and propyl paraben. Heat and maintain 70° C. with moderate agitation for 30 minutes. Add the water phase to the oil phase and agitate moderately. Add titanium dioxide and mix for 60 minutes. Cool batch slowly to 55° C. add the sodium lactate (60%) and continue to cool slowly with agitation to room temperature.

EXAMPLE 2 - CREAM EMULSION

| | Concentrate | % w/w |
|---|---|---|
| A. | Cyproterone acetate | 2.2 |
| | Stearic acid XXX | 7.6 |
| | Amerchol L-101 (mineral oil and lanolin alcohol)* | 5.0 |
| | Modulan (acetylated lanolin)* | 2.0 |
| | Cetyl alcohol | 3.0 |
| | Propyl Parasept | 0.1 |
| B. | Glycerin | 4.0 |
| | Methyl Paraben | 0.15 |
| | Water | 75.95 |

*Amerchol Corp., Edison, New Jersey

PROCEDURE

Combine (A) ingredients and heat to 70° C. Combine (B) ingredients separately and heat to 72° C. Add (B) to (A) with rapid stirring, then cool to room temperature.

EXAMPLE 3 - AEROSOL SPRAY

| Concentrate | | % w/w |
|---|---|---|
| A. | Magnesium aluminum silicate (Veegum K)* | 1.5 |
|  | Propylene glycol | 3.0 |
|  | Water | 86.0 |
| B. | Chlormadinone acetate | 2.2 |
|  | Diethylene glycol monostearate s.e. | 3.0 |
|  | Silicon 556 Fluid | 1.0 |
|  | Cetyl alcohol | 0.5 |
|  | Acetylated lanolin alcohols | 2.0 |
|  | Preservative | 0.2 |

*R. T. Vanderbilt Co., Norwalk, Conn.

PROCEDURE

Add the Veegum to water slowly with rapid agitation, until smooth. Add remaining (A) ingredients and heat to 80° C. Combine (B) ingredients and heat to 75° C. Add (A) to (B) with mixing and cool to room temperature. Package as an aerosol by combining 90 parts of concentrate with 10 parts of hydrocarbon propellent A-46.

EXAMPLE 4 - AEROSOL FOAM

| Concentrate | | % w/w |
|---|---|---|
| A. | Progesterone | 2.0 |
|  | Cyproterone acetate | 0.2 |
|  | Cetyl alcohol | 5.2 |
|  | Polyoxyethylene (40) monostearate (Myrj 52)* | 3.0 |
| B. | Propylene glycol | 4.0 |
|  | Water | 85.4 |
|  | Preservative | 0.2 |

*ICI Americas, Inc., Wilmington, Del.

PROCEDURE

Combine (A) ingredients and heat to 70° C. Combine (B) ingredients separately and heat to 72° C. Add (B) to (A) with mixing and cool to room temperature. Package as aerosol using a ratio of 7 parts hydrocarbon propellent A-31 to 93 parts of concentrate.

EXAMPLE 5 - ALCOHOL SOLUTION

| Concentrate | % w/w |
|---|---|
| 17α-propyltestosterone | 2.2 |
| Propylene glycol | 4.0 |
| Dimethicone | 1.0 |
| SDA-40 Alcohol | 92.8 |

PROCEDURE

Combine ingredients with mixing and package.

What is claimed is:

1. The process of reducing the rate and altering the character toward the vellus state of androgen-stimulated beard hair growth in intact, sexually mature males which comprises the step of applying to the skin a composition containing an effective amount of a material selected from the group consisting of 5-alpha-reductase inhibitors, cytoplasmic androgen receptor binding agents, and combinations thereof.

2. The process as described in claim 1 in which the 5-alpha-reductase inhibitor is selected from the group consisting of progesterone, (5α,20-R)-4-diazo-21-hydroxy-20-methyl-pregnan-3-one, (4R)-5,10-seco-19-norpregna-4,5-diene-3,10,20-trione, 4-androstene-3-one-17β-carboxylic acid, and it methyl ester, 17β-N,N-diethylcarbamoyl-4-methyl-4-aza-5α-androstane-3-one, 11α-hydroxy-progesterone, 17α-hydroxy-progesterone, 20α-hydroxy-progesterone, and combinations thereof.

3. The process as described in claim 2 resulting in the application of from about 10 to 10,000 micrograms of 5-alpha-reductase inhibitor per square centimeter of skin.

4. The process as described in claim 2 resulting in the application of from about 100 to 1,000 micrograms of 5-alpha-reductase inhibitor per square centimeter of skin.

5. The process as described in claim 1 in which the cytoplasmic androgen receptor binding agent is selected from the group containing of cyproterone acetate, chlormadinone acetate, 17α-propyltestosterone, 17α-allyltestosterone,α,α,α-trifluoro-2-methyl-4'-nitro-m-propionotoluidide, 6α-bromo-17β-hydroxy-17α-methyl-4-oxa-5α-androstane-3-one, 17β-acetoxy-4α,5-cyclo-A-homo-B-nor-5α-androst-1-ene-3-one, spironolactone, and combinations thereof.

6. The process as described in claim 5 resulting in the application of from about 0.1 to about 5,000 micrograms of the cytoplasmic androgen receptor binding agent per square centimeter of skin.

7. The process as described in claim 5 resulting in the application of from about 1.0 to 500 micrograms of cytoplasmic androgen receptor binding agent per square centimeter of skin.

8. The process as described in claim 1 in which a 5-alpha-reductase inhibitor is used along with a cytoplasmic androgen receptor binding agent.

9. The process as described in claim 8 in which the 5-alpha-reductase inhibitor is selected from the group consisting of progesterone, (5α,20-R)-4-diazo-21-hydroxy-20-methylpregnan-3-one, (4R)-5,10-seco-19-norpregna-4,5-diene-3,10,20-trione, 4-androstene-3-one-17β-carboxylic acid, and its methyl ester, 17β-N,N-diethylcarbamoyl-4-methyl-4-aza-5α-androstane-3-one, 11α-hydroxy-progesterone, 17β-hydroxy-progesterone, and 20α-hydroxy-progesterone, and combinations thereof, and in which the cytoplasmic androgen receptor binding agent is selected from the group consisting of cyproterone acetate, chlormadinone acetate, 17α-propyl-testosterone, 17α-allyltestosterone,α,α,α-trifluoro-2-methyl-4'-nitro-m-propionotoluidide, 6α-bromo-17β-hydroxy-17α-methyl-4-oxa-5α-androstane-3-one, 17β-acetoxy-4α,5-cyclo-A-homo-B-nor-5α-androst-1-ene-3-one, spironolactone, and combinations thereof.

10. The process as described in claim 9 resulting in the application of from about 10 to about 10,000 micrograms of 5-alpha-reductase inhibitor per square centimeter of skin and resulting in the application of from about 0.1 to about 5,000 micrograms of the cytoplasmic androgen receptor binding agent per square centimeter of skin.

11. The process as described in claim 9 resulting in the application of from about 100 to about 1,000 micrograms of 5-alpha-reductase inhibitor per square centimeter of skin and resulting in the application of from about 1.0 to 500 micrograms of cytoplasmic androgen receptor binding agent per square centimeter of skin.

12. A topical composition for reducing the rate and altering the character toward the vellus state of androgen-stimulated hair growth comprising a 5-alpha-reductase inhibitor selected from the group consisting of progesterone, 4-androstene-3-one-17β-carboxylic acid, and combinations thereof, and a cytoplasmic androgen receptor binding agent selected from the group consisting of 17 -propyltestosterone, 17-allyltestosterone, and combinations thereof, said 5-alpha-reductase inhibitor and said cytoplasmic androgen receptor binding agent being formulated in a dermatologically acceptable carrier, the concentrations of said 5-alpha-reductase inhibitor and said cytoplasmic androgen receptor binding agent each being from about 0.1% to about 10.0% by weight of the composition.

13. The composition as described in claim 12 in which the concentration of said 5-alpha-reductase inhibitor is from 0.5 to about 5.0% by weight of the composition and in which the concentration of said cytoplasmic androgen receptor binding agent is from about 0.02 to about 0.5% by weight of the composition.

14. A process for reducing the forces required to cut androgen-stimulated beard hair in intact, sexually mature males which comprises the step of applying to the skin a composition containing an effective amount of a material selected from the group consisting of 5-alpha-reductase inhibitors, cytoplasmic androgen receptor binding agents, and combinations thereof.

15. The process as described in claim 14 in which the 5-alpha-reductase inhibitor is selected from the group consisting of progesterone, (5α,20-R)-4-diazo-21-hydroxy-20-methyl-pregnan-3-one, (4R)-5,10-seco-19-norpregna-4,5-diene-3,10,20-trione, 4,androstene-3-one-17β-carboxylic acid, and its methyl ester, 17β-N,N-diethyl-carbamoyl-4-methyl-4-aza-5α-androstane-3-one, 11α-hydroxy-progesterone, 17α-hydroxy-progesterone, 20α-hydroxy-progesterone, and combinations thereof.

16. The process as described in claim 15 resulting in the application of from about 10 to 10,000 micrograms of 5-alpha-reductase inhibitor per square centimeter of skin.

17. The process as described in claim 15 resulting in the application of from about 100 to 1,000 micrograms of 5-alpha-reductase inhibitor per square centimeter of skin.

18. The process as described in claim 14 in which the cytoplasmic androgen receptor binding agent is selected from the group consisting of cyproterone acetate, chlormadinone acetate, 17α-propyltestosterone, 17α-allyltestosterone,α,α,α-trifluoro-2-methyl-4'-nitro-m-propionotoluidide, 6α-bromo-17β-hydroxy-17α-methyl-4-oxa-5α-androstane-3-one, 17β-acetoxy-4α,5-cyclo-A-homo-B-nor-5α-androst-1-ene-3-one, spironolactone, and combinations thereof.

19. The process as described in claim 18 resulting in the application of from about 0.1 to about 5,000 micrograms of the cytoplasmic androgen receptor binding agent per square centimeter of skin.

20. The process as described in claim 18 resulting in the application of from about 1.0 to 500 micrograms of cytoplasmic androgen receptor binding agent per square centimeter of skin.

21. The process as described in claim 14 in which the 5-alpha-reductase inhibitor is used along with a cytoplasmic androgen receptor binding agent.

22. The process as described in claim 21 in which the 5-alpha-reductase inhibitor is selected from the group consisting of progesterone, (5α,20-R)-4-diazo-21-hydroxy-20-methylpregnan-3-one, (4R)-5,10-seco-19-norpregna-4,5-diene-3,10,20-trione, 4-androstene-3-one-17β-carboxylic acid, and its methyl ester, 17β-N,N-diethylcarbamoyl-4-methyl-4-aza-5α-androstane-3-one, 11α-hydroxy-progesterone, 17α-hydroxy-progesterone, and 20α-hydroxy-progesterone, and combinations thereof, and in which the cytoplasmic androgen receptor binding agent is selected from the group consisting of cyproterone acetate, chlormadinone acetate, 17α-propyl-testosterone, 17α-allyltestosterone,α,α,α,-trifluoro-2-methyl-4'-nitro-m-propionotoluidide, 6α-bromo-17β-hydroxy-17α-methyl-4-oxa-5α-androstane-3-one, 17β-acetoxy-4α,5-cyclo-A-homo-B-nor-5α-androst-1-ene-3-one, spironolactone, and combinations thereof.

23. The process as described in claim 22 resulting in the application of from about 10 to about 10,000 micrograms of 5-alpha-reductase inhibitor per square centimeter of skin and resulting in the application of from about 0.1 to about 5,000 micrograms of the cytoplasmic androgen receptor binding agent per square centimeter of skin.

24. The process as described in claim 22 resulting in the application of from about 100 to about 1,000 micrograms of 5-alpha-reductase inhibitor per square centimeter of skin and resulting in the application of from about 1.0 to 500 micrograms of cytoplasmic androgen receptor binding agent per square centimeter of skin.

25. A topical composition for reducing the forces required to cut androgen-stimulated beard hair in intact, sexually mature males comprising a 5-alpha-reductase inhibitor selected from the group consisting of progesterone, 4-androstene-3-one-17α-carboxylic acid, and combinations thereof, and a cytoplasmic androgen receptor binding agent selected from the group consisting of 17α-propyltestosterone, 17α-allyltestosterone, and combinations thereof, said 5-alpha-reductase inhibitor and said cytoplasmic androgen receptor binding agent being formulated in a dermatologically acceptable carrier, the concentrations of said 5-alpha-reductase inhibitor and said cytoplasmic androgen receptor binding agent each being from about 0.1% to about 10.0% by weight of the composition.

26. The composition as described in claim 25 in which the concentration of said 5-alpha-reductase inhibitor is from 0.5 to about 5.0% by weight of the composition and in which the concentration of said cytoplasmic androgen receptor binding agent is from about 0.02 to about 0.5% by weight of the composition.

* * * * *